United States Patent [19]

Kawano et al.

[11] 4,312,777
[45] Jan. 26, 1982

[54] EMULSIFIER COMPOSITION

[75] Inventors: Junichi Kawano, Sakura; Hisao Tsutsumi, Miyashiro; Toshiaki Utsugi, Tokyo, all of Japan

[73] Assignee: Kao Soap Co., Ltd., Tokyo, Japan

[21] Appl. No.: 98,687

[22] Filed: Nov. 29, 1979

[30] Foreign Application Priority Data

Dec. 14, 1978 [JP] Japan ................................ 53-155509

[51] Int. Cl.$^3$ ............................................. B01F 17/00
[52] U.S. Cl. .................................... 252/352; 252/356
[58] Field of Search ............... 252/352, 356, 312, 314, 252/DIG. 1, DIG. 7; 424/170

[56] References Cited

U.S. PATENT DOCUMENTS

| 3,419,665 | 12/1968 | Lachampt et al. | 252/356 |
| 3,442,842 | 5/1969 | Bonin | 252/356 |
| 3,776,857 | 12/1973 | Lindner | 252/356 |
| 3,926,840 | 12/1975 | Wendler | 252/356 |
| 3,954,658 | 5/1976 | Tsutsumi et al. | 252/356 |
| 4,097,403 | 6/1978 | Tsutsumi et al. | 252/356 |

Primary Examiner—J. L. Barr
Attorney, Agent, or Firm—Oblon, Fisher, Spivak, McClelland & Maier

[57] ABSTRACT

An emulsifier composition comprising a polyoxyethylene sorbitol fatty acid ester and a multivalent metal salt of a fatty acid is effective in stabilizing water-in-oil type emulsions.

5 Claims, No Drawings

EMULSIFIER COMPOSITION

BACKGROUND OF THE INVENTION

1. Field of the Invention

This invention relates to a novel emulsifying composition of a water-in-oil type.

2. Description of the Prior Art

As is generally known, emulsions of a water-in-oil (W/O) type consisting of water dispersed in an oil phase possess a higher antibacterial activity than those of an oil-in-water (O/W) type in which the phases are reversed. Another advantage of the W/O emulsions is easy retention of water in the emulsions. Because of these substantial advantages, the W/O emulsions have found application to cosmetics and further to oils for use in textile finishing, metal processing and similar treatment.

However, the known W/O emulsions suffer from some defects whereby the use of such emulsions is currently being restricted as compared to O/W emulsions.

In general, the breaking of emulsions is due to aggregation of particles with subsequent coalescence of the aggregates. Since the rate of aggregation is greater than that of coalescence, it is necessary to prevent aggregation at an initial stage in order to prevent breaking of the emulsions. In the O/W emulsions where water is the dispersion medium or continuous liquid, water is separated from an aggregated phase. However, the water thus separated, if in small quantities, does not exert any adverse effects upon the properties of the O/W emulsions because it is so volatile as to be substantially removed from the emulsions. In contrast to the O/W emulsions, the separation of oil takes place as a consequence of aggregation in the W/0 emulsions in which oil is the disperse liquid or continuous phase. The oil once separated, even if in small quantities, is not readily volatile but becomes virtually present in the emulsions. This is particularly detrimental to the appearance or commercial acceptance of the W/O emulsions.

Such defects make it difficult to prepare W/O emulsions which are stable over a wide range of temperatures. Furthermore, the absence of any suitable emulsifying agents creates an obstacle to surmounting these defects.

In view of the disadvantages possessed by the existing W/O emulsions, the present inventors have made intensive studies of a variety of compounds or emulsifying agents which are effective in stabilizing W/O emulsions. From these studies, it has been found that polyoxyethylene sorbitol fatty acid esters of a specific class in combination with multivalent metal salts of fatty acids of a specific class achieve the above desired properties and give the best results.

SUMMARY OF THE INVENTION

It is an object of this invention to provide an emulsifying composition of a W/O type which is substantially devoid of the undesirable effects of the conventional W/O emulsions.

It is another object of the invention to provide an emulsifying composition of a W/O type which comprises a polyoxyethylene sorbitol fatty acid ester and a multivalent metal salt of a fatty acid and which exhibits stability characteristics over a wide range of temperatures.

DETAILED DESCRIPTION OF THE PREFERRED EMBODIMENTS

The present invention provides an emulsifying composition of a water-in-oil type comprising a polyoxyethylene sorbitol fatty acid ester represented by the formula (I),

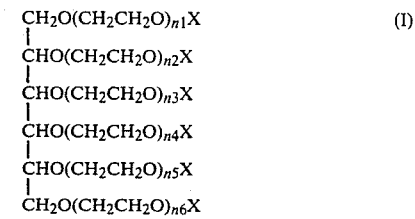

wherein two to six X's each represent a saturated or unsaturated acyl group having 12 to 20 carbon atoms, the remainder of the X's being hydrogen atoms, and N1, n2, n3, n4, n5 and n6 are each integers of 0 to 10, whose sum ranges from 6 to 10, and a multivalent metal salt of a saturated or unsaturated fatty acid having 12 to 22 carbon atoms.

Suitable polyoxyethylene sorbitol fatty acid esters of the formula (I) which are useful in the invention include, for example, esters such as of oleic ester, stearic ester, myristic ester, palmitic ester and lauric ester of polyoxythylene sorbitol each having an average addition mole number of 6 to 10 of polyoxyethylene relative to 1 mole of the sorbitol.

Suitable multivalent metal salts of saturated or unsaturated fatty acids which are useful in the invention include, for example, divalent, trivalent and tetravelent metal salts of fatty acids such as of oleic acid, palmitic acid, myristic acid, stearic acid and lauric acid, which metal salts are those of calcium, magnesium, zinc and aluminum. Of these metal salts, particularly preferable are aluminum monostearate, aluminum distearate, aluminum tristearate, aluminum monooleate, aluminum dioleate, aluminum trioleate, aluminum monopalmitate, aluminum dipalmitate, aluminum tripalmitate, aluminum monomyristate, aluminum dimyristate, aluminum trimyristate, magnesium monostearate, magnesium distearate, magnesium monooleate, magnesium dioleate, magnesium monopalmitate, magnesium dipalmitate, magnesium monomyristate, magnesium dimyristate, magnesium monolaurate and magnesium dilaurate.

According to the invention, it is preferable that the multivalent metal salt of the fatty acid, described above, be prepared in the emulsifying composition by mixing a water-soluble, inorganic multivalent metal salt with a monovalent cationic salt such as the sodium, potassium, ammonium, triethanolamine or diethanolamine salt of the fatty acid. In such instance, suitable water-soluble multivalent metal salts include, for example, calcium chloride, magnesium chloride, magnesium sulfate, zinc chloride, aluminum chloride, aluminum sulfate and alum. Those multivalent metal salts of the fatty acids may be utilized which have been previously prepared by any conventional method known in the art.

Suitable emulsifying agents which are useful in the invention can be produced in any conventional manner, for example, by mixing and stirring under heating conditions polyoxyethylene sorbitol fatty acids in amounts of 65 to 99.5% by weight, preferably 80 to 99% by weight, and multivalent metal salts of fatty acids in amounts of 35 to 0.5% by weight, preferably 20 to 1% by weight.

The emulsifying agents thus obtained are highly effective in producing W/O emulsions which have superior and prolonged stability over a wide range of temperatures, particularly when applied to various oil-water systems including hydrocarbons such as liquid paraffins, squalane, vaseline, mineral oils and the like; animal and vegetable oils each having a fatty acid glyceride as an essential component; higher fatty acids; higher alcohols; esters such as isopropyl myristate; and silicone oils.

This invention will now be described with reference to certain specific Examples which are provided for purposes of illustration only and are not intended to be construed as limiting.

EXAMPLE 1

Sample emulsifying agents were prepared by mixing polyoxyethylene sorbitol fatty acid esters (I) with multivalent metal salts of fatty acids (II). Thereafter, mixtures each having a formulation listed below and containing one of the sample emulsifying agents were heated up to 70° C. and emulsified with stirring to obtain emulsions. Each of the emulsions was determined and graded in respect of its type of emulsification by the electrical conductivity, particle diameter by microscopic examination and stability by the degree of separation after standing for 15 days at −15° C., +20° C. and +50° C., respectively, with the results tabulated in Table 1.

Formulation:

| Liquid paraffin | 30 parts |
|---|---|
| Water | 65 |
| Emulsifying agent | 5 |

Esterification:
Average number of hydroxy groups esterified out of the six hydroxy groups in a polyoxyethylene sorbitol.

Grading Notations of Stability:
− :Not separated
+ :Slightly separated oil
+ + :Separated into two layers of a cream phase and an aggregated phase (oil)
+ + + :Separated into three layers of a cream phase, an aggregated phase (oil) and a coalescent phase (water)
+ + + + :Separated into two layers of an aggregated phase (oil) and a coalescent phase (water), with eventual disappearance of a cream phase
X:Coagulated As is clear from the results shown in Table 1, the polyoxyethylene sorbitol fatty acid esters when combined with the multivalent metal salts of the fatty acids can produce W/O emulsions which are stable over a wide range of temperatures.

EXAMPLE 2

Sample emulsifying agents were prepared by mixing polyoxyethylene sorbitol fatty acid esters with multivalent metal salts of fatty acids in a weight ratio of 80:20. For purposes of comparison, additional emulsifying agents were prepared either by employing other fatty acid esters alone or by mixing such esters with multivalent metal salts of fatty acids in a weight ratio of 80:20. Thereafter, emulsions were obtained using these two groups of sample emulsifying agents. Each of the emulsions was determined and graded in respect of its type of emulsification, particle diameter and stability after standing for 15 days at five different temperatures.

The same determination procedure and grading notations as in Example 1 were applied, with the results tabulated in Table 2.

TABLE 1

| | Emulsifying agents | (I)/(II) | Type of emulsification | Particle diameter ($\mu$) | Stability (After 15 days) −15° C. | 20° C. | 50° C. |
|---|---|---|---|---|---|---|---|
| Present invention | Polyoxyethylene(7)sorbitol myristic acid ester (esterification: 4.0) (I) | 98/2 | W/O | 1> | − | − | − |
| | | 80/20 | W/O | 1> | − | − | − |
| | Aluminum monostearate (II) | 70/30 | W/O | 1> | − | − | − |
| | Polyoxyethylene(6)sorbitol lauric acid ester (esterification: 5.0) (I) | 90/10 | W/O | 1> | − | − | − |
| | Magnesium monolaurate (II) | 85/15 | W/O | 1> | − | − | − |
| Control | Polyoxyethylene(7)sorbitol myristic ester (esterification: 4.0) | | W/O | 1> | + + | − | + + |
| | Aluminum monostearate | | W/O | 10< | + + | + + + | + + + + |
| | Polyoxyethylene(6)sorbitol lauric acid ester (esterification: 5.0) | | W/O | 2-5 | + + + | − | + + |
| | Magnesium monolaurate | | W/O | 10< | + | + + + | + + + + |

TABLE 2

| | Emulsifying agents Ester | Salt | Type of emulsification | Particle diameter ($\mu$) | Stability (After 15 days) −15° C. | −5° C. | 20° C. | 40° C. | 50° C. |
|---|---|---|---|---|---|---|---|---|---|
| Present invention | Polyoxyethylene(7)-sorbitol oleic acid ester (esterification: 4.0) | Aluminum monostearate | W/O | 1> | − | − | − | − | − |
| | Polyoxyethylene(10)-sorbitol oleic acid ester (esterification: 3.0) | Calcium monostearate | W/O | 1> | − | − | − | − | − |

TABLE 2-continued

| Emulsifying agents | | Type of emulsification | Particle diameter (μ) | Stability (After 15 days) | | | | |
|---|---|---|---|---|---|---|---|---|
| Ester | Salt | | | −15° C. | −5° C. | 20° C. | 40° C. | 50° C. |
| Polyoxyethylene(6)-sorbitol lauric acid ester (esterification: 3.0) | Magnesium monolaurate | W/O | 1.5 | − | − | − | − | − |
| Control Sorbitan monostearate | Aluminum monostearate | W/O | 10< | +++ | ++ | ++ | +++ | +++ |
| Sorbitan monostearate | Calcium monostearate | W/O | 10< | +++ | ++ | ++ | +++ | +++ |
| Polyoxyethylene(6)-stearate | Aluminum monostearate | W/O | 10< | +++ | + | + | +++ | +++ |
| Polyoxyethylene(2)-laurate | Aluminum monostearate | W/O | 10< | +++ | + | ++ | +++ | +++ |
| Polyoxyethylene(3)-stearate | Aluminum monostearate | W/O | 10< | +++ | + | ++ | +++ | +++ |
| Glycerol monostearate | Aluminum monostearate | W/O | 10< | X | +++ | +++ | +++ | ++++ |
| Sorbitan monostearate | | W/O | 10< | +++ | ++ | ++ | +++ | +++ |
| Sorbitan tristearate | | W/O | 10< | +++ | ++ | ++ | +++ | +++ |
| Polyoxyethylene(6)stearate | | W/O | 10< | +++ | + | + | +++ | +++ |
| Polyoxyethylene(2)laurate | | W/O | 10< | +++ | + | ++ | +++ | +++ |
| Polyoxyethylene(3)stearate | | W/O | 10< | +++ | + | ++ | +++ | +++ |
| Glycerine monostearate | | W/O | 10< | X | +++ | +++ | +++ | ++++ |

EXAMPLE 3

Sample emulsifying agents were prepared by mixing polyoxyethylene sorbitol fatty acid esters (I) with multivalent metal salts of fatty acids (II) in a weight ratio of 84:16. Thereafter, mixtures each having a formulation listed below and containing one of the sample emulsifying agents were treated in the same manner as in Example 1 to obtain emulsions. Each of the emulsions was determined and graded in respect of its type of emulsification, particle diameter and stability, with the results tabulated in Table 3.

The same determination procedure and grading notations as in Example 1 were applied, but the water and oil phases should be reversed in the notations in the case where the emulsions were of an O/W type.

Formulation:

| Liquid paraffin | 30 parts |
|---|---|
| Water | 65 |
| Emulsifying agent | 5 |

TABLE 3

| | Emulsifying agents | | Type of emulsification | Particle diameter (μ) | Stability (After 15 days) | | | | |
|---|---|---|---|---|---|---|---|---|---|
| | I | (II) | | | −15° C. | −5° C. | 20° C. | 40° C. | 55° C. |
| Present invention | Polyoxyethylene(6)-sorbitol oleic acid ester (esterification: 3.0) | Aluminum distearate | W/O | 1> | − | − | − | − | − |
| | Polyoxyethylene(7)-sorbitol oleic acid ester (esterification: 6.0) | Aluminum monostearate | W/O | 1> | − | − | − | − | − |
| | Polyoxyethylene(7)-sorbitol oleic acid ester (esterification: 4.0) | Calcium monostearate | W/O | 1> | − | − | − | − | − |
| | Polyoxyethylene(10)-sorbitol oleic acid ester (esterification: 4.0) | Magnesium monostearate | W/O | 1.5 | − | − | − | − | − |
| | Polyoxyethylene(6)-sorbitol oleic acid ester (esterification: 2.0) | Zinc monolaurate | W/O | 1> | − | − | − | − | − |
| | Polyoxyethylene(7)-sorbitol stearic acid ester (esterification: 2.0) | Aluminum monostearate | W/O | 1-2 | − | − | − | − | − |
| | Polyoxyethylene(6)-sorbitol lauric acid ester (esterification: 3.0) | Magnesium monolaurate | W/O | 1.5 | − | − | − | − | − |
| | Polyoxyethylene(10)-sorbitol lauric acid ester (esterification: 6.0) | Aluminum dipalmitate | W/O | 2-3 | − | − | − | − | − |
| Control | Polyoxyethylene(30)- | Aluminum | O/W | 2-5 | X | + | − | − | ++ |

TABLE 3-continued

| Emulsifying agents | | Type of emulsifi- | Particle diameter | Stability (After 15 days) | | | | |
|---|---|---|---|---|---|---|---|---|
| I | (II) | cation | (μ) | −15° C. | −5° C. | 20° C. | 40° C. | 55° C. |
| sorbitol oleic acid ester (esterification: 4.0) | monostearate | | | | | | | |
| Polyoxyethylene(15)-sorbitol oleic acid ester (esterification: 1.0) | Aluminum distearate | O/W | 5-8 | X | − | − | ++ | +++ |
| Polyoxyethylene(7)-sorbitol lauric acid ester (esterification: 1.0) | Aluminum monostearate | O/W | 5-8 | X | +++ | +++ | +++ | ++++ |
| Polyoxyethylene(7)-sorbitol capric acid ester (esterification: 4.0) | Aluminum monostearate | W/O | 10< | X | ++ | ++++ | ++++ | ++++ |
| Polyoxyethylene(12)-sorbitol capric acid ester (esterification: 1.0) | Aluminum monostearate | O/W | 10< | X | + | ++ | +++ | ++++ |
| Polyoxyethylene(7)-sorbitol oleic acid ester (esterification: 4.0) | Aluminum dicaprate | W/O | 10< | X | +++ | +++ | +++ | ++++ |
| Polyoxyethylene(15)-sorbitol oleic acid ester (esterification: 4.0) | Sodium stearate | O/W | 1-2 | X | − | − | − | − |
| Polyoxyethylene(12)-sorbitol oleic acid ester (esterification: 3.0) | Sodium oleate | O/W | 2-5 | X | − | − | − | +++ |
| Polyoxyethylene(10)-sorbitol oleic acid ester (esterification: 6.0) | Sodium caprate | W/O | 10< | X | ++++ | ++++ | ++++ | ++++ |

EXAMPLE 4

Mixtures each having a formulation listed below and containing one of the emulsifying agents which were useful in the invention were treated in the same manner as in Example 1 to obtain emulsions. For purposes of comparison, a different group of emulsifying agents were tested which had been either conventionally acceptable compounds as emulsifiers or mixtures of such compounds and 14% multivalent metal salts of fatty acids. Each of the emulsions was determined and graded in respect of its type of emulsification, particle diameter and stability, with the results tabulated in Table 4.

The same determination procedure and grading notations as in Example 1 were applied, but the water and oil phases should be reversed in the notations in the case where the emulsions were of an O/W type.

Formulation:

| Liquid paraffin | 30 parts |
|---|---|
| Water | 65 |
| Emulsifying agent | 5 |

TABLE 4

| | Emulsifying agents | | Type of emulsifi- | Particle diameter | Stability (After 15 days) | | | | |
|---|---|---|---|---|---|---|---|---|---|
| | Esters | Fatty acid salts | cation | (μ) | −15° C. | −5° C. | 20° C. | 40° C. | 55° C. |
| Present invention | Polyoxyethylene(7)-sorbitol oleic acid ester (esterification: 4.0) | 14% Aluminum monostearate | W/O | 1> | − | − | − | − | − |
| | Polyoxyethylene(10)-sorbitol oleic acid ester (esterification: 3.0) | 14% Calcium monostearate | W/O | 1> | − | − | − | − | − |
| Control | Polyoxyethylene(5)-sorbitan monooleate | None | O/W | 1-2 | X | − | − | − | +++ |
| | Polyoxyethylene(5)-sorbitan monooleate | 14% Aluminum monostearate | W/O | 1-2 | +++ | + | + | ++ | +++ |
| | Sorbitan monooleate | None | W/O | 2-5 | + | − | − | ++ | +++ |
| | Sorbitan monooleate | 14% Aluminum monostearate | W/O | 1> | − | − | − | + | +++ |
| | Sorbitan sesquioleate | None | W/O | 2-5 | − | − | − | +++ | +++ |
| | Sorbitan sesquioleate | 14% Aluminum monostearate | W/O | 2-5 | − | − | − | + | +++ |
| | Sorbitan trioleate | None | W/O | 5-8 | ++ | − | − | +++ | +++ |
| | Sorbitan trioleate | 14% Aluminum | W/O | 2-5 | − | − | − | +++ | +++ |

TABLE 4-continued

| Emulsifying agents | | Type of emulsification | Particle diameter (μ) | Stability (After 15 days) | | | | |
|---|---|---|---|---|---|---|---|---|
| Esters | Fatty acid salts | | | −15° C. | −5° C. | 20° C. | 40° C. | 55° C. |
| | monostearate | | | | | | | |
| Sorbitan monostearate | None | W/O | 10< | +++ | ++ | ++ | +++ | +++ |
| Sorbitan monostearate | 14% Aluminum monostearate | W/O | 10< | +++ | ++ | ++ | +++ | +++ |
| Sorbitan tristerate | None | W/O | 10< | +++ | ++ | ++ | +++ | +++ |
| Sorbitan tristerate | 14% Calcium monostearate | W/O | 10< | +++ | ++ | ++ | +++ | +++ |
| Polyoxyethylene(3)-stearate | None | W/O | 10< | +++ | + | + | +++ | +++ |
| Polyoxyethylene(3)-stearate | 14% Aluminum monostearate | W/O | 10< | +++ | + | + | +++ | +++ |
| Polyoxyethylene(5)-oleate | None | O/W | 2-5 | X | − | − | − | + |
| Polyoxyethylene(5)-oleate | 14% Aluminum monostearate | W/O | 10< | +++ | ++ | ++ | +++ | +++ |
| Glycerol monostearate | None | W/O | 10< | X | +++ | +++ | +++ | ++++ |
| Glycerol monostearate | 14% Aluminum monostearate | W/O | 10< | X | +++ | +++ | +++ | ++++ |
| Glycerol dioleate | None | W/O | 5-8 | − | − | − | ++ | +++ |
| Glycerol dioleate | 14% Aluminum monostearate | W/O | 5-8 | − | − | − | ++ | +++ |
| Polyoxyethylene(2)-lauryl ether | None | W/O | 10< | +++ | + | ++ | +++ | +++ |
| Polyoxyethylene(2)-lauryl ether | 14% Aluminum monostearate | W/O | 10< | +++ | + | ++ | +++ | +++ |
| Polyoxyethylene(3)-stearyl ether | None | W/O | 10< | +++ | + | ++ | +++ | +++ |
| Polyoxyethylene(3)-stearyl ether | 14% Aluminum monostearate | W/O | 10< | +++ | + | ++ | +++ | +++ |
| Polyoxyethylene(5)-oleyl ether | None | O/W | 5-8 | X | − | − | − | +++ |
| Polyoxyethylene(5)-oleyl ether | 14% Aluminum monostearate | W/O | 10< | X | +++ | +++ | +++ | ++++ |
| Sugar ester (disterate) | None | W/O | 2-5 | X | − | − | +++ | +++ |
| Sugar ester (disterate) | 14% Aluminum monostearate | W/O | 2-5 | − | − | − | +++ | +++ |
| Oleyl sesquiphosphate | None | W/O | 5-8 | + | − | − | +++ | +++ |
| Oleyl sesquiphosphate | 14% Aluminum monostearate | W/O | 2-5 | + | − | − | +++ | +++ |
| Lanolin alcohol | None | W/O | 10< | X | − | − | +++ | ++++ |
| Lanolin alcohol | 14% Aluminum monostearate | W/O | 10< | X | − | − | ++ | ++ |

EXAMPLE 5

Cosmetic

Mixtures each having a formulation listed below were heated at 70° C. and mixed with stirring to obtain cosmetics. Each of the cosmetics was determined and graded in respect of its type of emulsification by electrical conductivity, particle diameter by microscopic examination and stability by the degree of separation after standing for 15 days at three different temperatures, with the results tabulated in Table 5.

The same grading notations as in Example 1 were applied for stability determination.

Formulation:

| | |
|---|---|
| Oil base (Olive oil) | 30% by weight |
| Emulsifying agent | 5 |
| Naturally occurring perfume | 0.2 |
| Water | 64.8 |

TABLE 5

| Emulsifying agents Weight ratios of compound (I) to compound (II) | Types of emulsification | Particle diameter (μ) | Stability (After 15 days) | | |
|---|---|---|---|---|---|
| | | | −15° C. | 40° C. | 50° C. |
| 100/0 | W/O | 1> | +++ | − | +++ |
| 99.5/0.5 | W/O | 1> | − | − | − |
| 98/2 | W/O | 1> | − | − | − |
| 80/20 | W/O | 1> | − | − | − |
| 70/30 | W/O | 1> | − | − | − |
| 65/35 | W/O | 1> | − | − | − |
| 60/40 | W/O | 1> | − | − | +++ |
| 0/100 | W/O | 10< | ++ | − | +++ |

Compound (I): Polyoxyethylene sorbitol oleic acid ester
addition mole number; 7
esterification: 4.1
Compound (II): Aluminum monostearate

EXAMPLE 6

W/O Type Metal Processing Oil

Starting Materials:

| | | |
|---|---|---|
| (1) | Spindle oil | 40 parts |
| (2) | Tallow | 12 |
| (3) | Polyoxyethylene(6)sorbitol oleic acid ester (esterification: 3) | 3 |
| (4) | Aluminum monostearate | 0.2 |

| | |
|---|---|
| (5) Water | 45 |

Preparation:

A mixture of (1) to (4) was heated at 65° to 70° C., to which was then added with stirring (5) which had been previously heated at the same temperature. After being emulsified, the resulting mixture was gradually cooled to obtain an oil.

The metal processing oil thus prepared exhibited excellent stability for a long period of time.

EXAMPLE 7

Rust Preventing Oil

Starting Materials:

| | |
|---|---|
| (1) Spindle oil | 46 parts |
| (2) Linseed oil | 18 |
| (3) Polyoxyethylene(7)sorbitol oleic acid ester (esterification: 4) | 4 |
| (4) Magnesium monostearate | 0.3 |
| (5) Lauryl phosphate | 2 |
| (6) Water | 30 |

Preparation:

A mixture of (1) to (5) was heated at 60° to 65° C., to which was then added with stirring (6) which had been previously heated at the same temperature. After being emulsified, the resulting mixture was gradually cooled to obtain an oil.

The rust preventing oil thus prepared exhibited excellent stability for a long period of time.

We claim:

1. An emulsifier composition of the water-in-oil type consisting essentially of 65 to 99.5% by weight of a polyoxyethylene sorbitol fatty acid ester represented by the following formula:

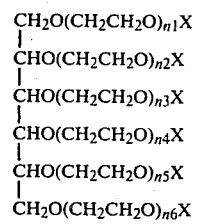

wherein two to six X's each represent a saturated or unsaturated acyl group having 12 to 20 carbon atoms, the remainder of the X's being hydrogen atoms, and n1, n2, n3, n4, n5 and n6 are each integers of 0 to 10, whose sum ranges from 6 to 10; and 35 to 0.5% by weight of a multivalent metal salt of a saturated or unsaturated fatty acid having 12 to 22 carbon atoms.

2. The emulsifying composition of claim 1, wherein said multivalent metal salt is selected from the group consisting of salts of calcium, magnesium, zinc and aluminum.

3. The emulsifying composition of claim 1 or 2, wherein said multivalent metal salt of a saturated or unsaturated fatty acid is formed by mixing a monovalent cationic salt of saturated or unsaturated fatty acid and a water-soluble, inorganic multivalent metal salt.

4. The emulsifying composition of claim 3, wherein said monovalent cationic salt is selected from the group consisting of salts of sodium, potassium, ammonium, triethanolamine and diethanolamine.

5. The emulsifying composition of claim 3, wherein said water-soluble multivalent metal salt is selected from the group consisting of magnesium chloride, magnesium sulfate, zinc chloride, aluminum chloride, aluminum sulfate and alum.

* * * * *